(12) United States Patent
Reed

(10) Patent No.: US 6,193,806 B1
(45) Date of Patent: Feb. 27, 2001

(54) DEVICE FOR TRANSMITTING AN IMPULSE FOR CLEANING SOFT CONTACT LENS

(76) Inventor: Larry F. Reed, 1300 Walter Smith Rd., Mobile, AL (US) 36695

( * ) Notice: Subject to any disclaimer, the term of this patent is extended or adjusted under 35 U.S.C. 154(b) by 0 days.

(21) Appl. No.: 09/347,725

(22) Filed: Jul. 6, 1999

(51) Int. Cl.⁷ ....................................................... B08B 3/10
(52) U.S. Cl. .................. 134/1; 134/254; 134/42; 134/117; 134/901
(58) Field of Search ........................... 134/1, 25.4, 42, 134/117, 140, 901

(56) References Cited

U.S. PATENT DOCUMENTS

| | | | |
|---|---|---|---|
| 3,291,458 | * | 12/1966 | Hamm .................................. 134/117 |
| 3,973,760 | * | 8/1976 | Browning et al. .................... 134/901 |
| 4,693,037 | * | 9/1987 | McNeil ................................. 134/117 |
| 4,852,594 | * | 8/1989 | Chen ..................................... 134/901 |
| 4,957,128 | * | 9/1990 | Chen ..................................... 134/140 |
| 5,129,410 | * | 7/1992 | Ifejika .................................... 134/32 |

* cited by examiner

*Primary Examiner*—Randy Gulakowski
*Assistant Examiner*—Saeed Chaudhry
(74) *Attorney, Agent, or Firm*—George L. Williamson

(57) ABSTRACT

A soft contact lens cleaning device is disclosed which imparts a high amplitude short duration mechanically generated force to the lenses while the lenses are stored within their standard storage case. The shock of the force dislodges protein, film and other buildups which become attached to the lens surface while being worn in the eyes of a user. Embodiments are disclosed comprising leaf, coil and torsional spring members along with a solenoid member.

15 Claims, 2 Drawing Sheets

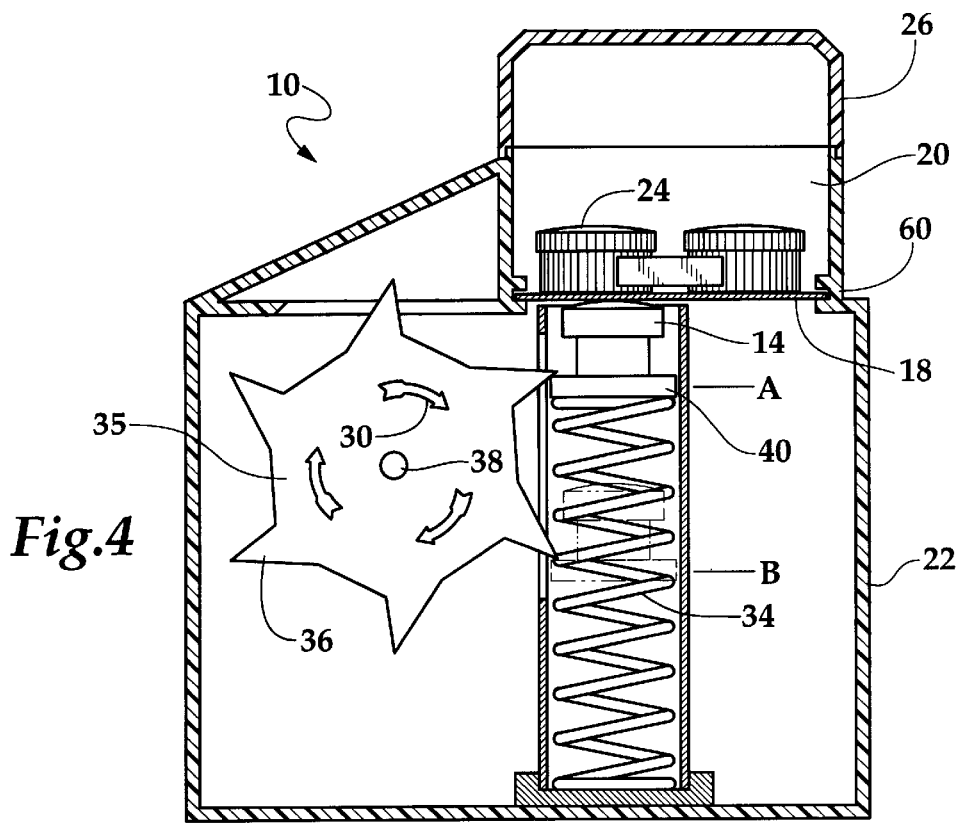
*Fig.4*
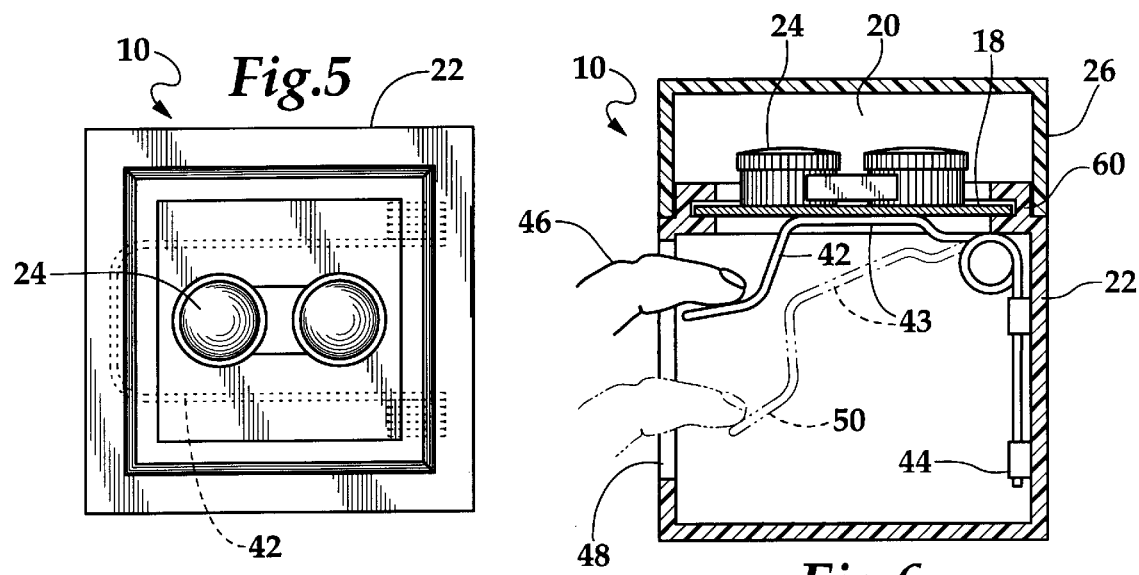
*Fig.5*
*Fig.6*
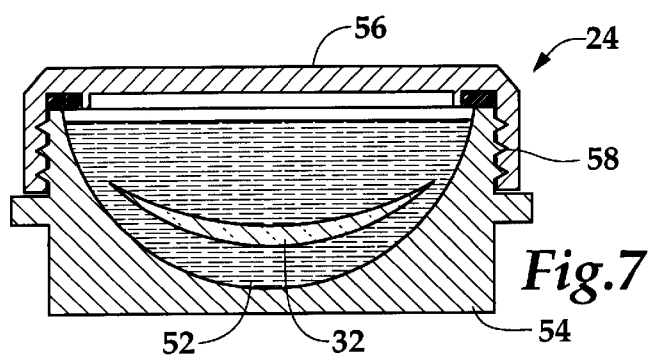
*Fig.7*

DEVICE FOR TRANSMITTING AN IMPULSE FOR CLEANING SOFT CONTACT LENS

BACKGROUND OF THE INVENTION

1. Field of the Invention

The present invention generally relates to methods for cleaning soft contact lenses and, more particularly, is concerned with a mechanical means for removing the various undesirable build-ups on disposable soft contact lenses surfaces which limit their usable life.

2. Description of the Prior Art

Devices for cleaning contact lens have been described in the prior art for removing build-ups, which can be protein or bacterial, which eventually occur on the lens surface which makes the lens uncomfortable to the wearer and at this point the lenses are generally discarded in favor of a new pair of lenses. However, none of the prior art devices disclose the unique features of the present invention.

The device in this invention forestalls these build-ups appreciably if not totally in many cases, thus extending the wearable life of disposable soft lenses.

In U.S. Pat. No. 4,965,904 dated Oct. 30, 1990, Tanaka, et al., disclosed a contact lens cleaning device comprising a ball, a vessel formed with a recessed chamber for housing the lens and the ball, and a vibrator for vibrating the vessel. The chamber has a bottom concave surface so curved that the lens is mounted in fact-to-face contact thereon. After the lens is sandwiched between the bottom concave surface of the chamber, the ball is cleaned when the vessel is vibrated by the vibrator.

In U.S. Pat. No. 4,957,128, dated Sep. 18, 1990, Chen disclosed a contact lens cleaner which includes a base, a vibrating plate mounted swingably on the base, a container mounted removably on the vibrating plate so as to receive an amount of a cleaning liquid and a contact lens therein, a motor disposed on the base so as to swing the vibrating plate, a cam member mounted rotatably on the base and having a cam surface which is engaged with the free end of the vibrating plate, and a resilient element biasing the free end of the vibrating plate toward the cam member. When the motor is started so as to rotate the cam member, the cam surface of the cam member pushes the free end of the vibrating plate to move in one direction, while the resilient element moves the free end of the vibrating plate in the opposite direction to engage with the cam surface of the cam member, so as to swing the vibrating plate, thereby rinsing the contact lens with the cleaning liquid.

In U.S. Pat. No. 4,697,605, dated Oct. 6, 1987, Yung disclosed a contact lens cleaning and disinfecting apparatus with a cavity in which a contact lens is to be cleaned by an aqueous non-chemosterilant liquid such as a saline solution. An ultra-sonic transducer applies vibrations to the cavity. The oscillator driving the transducer includes a transformer feedback circuit using one or more cores of high magnetic permeability and low core loss to give a stable resonant frequency. A timer may be driven from this resonant frequency. In one embodiment the cavity and the sealing cap may be removable together with the transducer from the rest of the housing of the apparatus so that lenses can be transported conveniently after cleaning and before use. According to another embodiment the waste heat from power transistors can be used to heat the cleaning liquid in the cavity.

In U.S. Pat. No. 4,607,652, dated Aug. 26, 1986, Yung disclosed a contact lens cleansing apparatus which comprises at least one cavity for containing a contact lens together with cleansing a liquid. An ultrasonic transducer supplies ultrasonic frequency mechanical vibrations to the liquid and lens contained in the cavity. Oscillating means for driving ultrasonic transducer at a substantially stable resonant frequency includes a dual ferrite core transformer feedback circuit which minimizes energy consumption. There is also a timer whose operation is controlled from the oscillating means. Simultaneous cleaning and sterilizing of a contact lens is achieved.

In U.S. Pat. No. 5,144,144, dated Sep. 1, 1992, Borovsky disclosed a contact lens cleaning and disinfecting system which is formed as a compact unit with an upper housing portion containing a UV lamp and a lower base portion containing a cleaning/disinfecting chamber which is filled with saline solution, a lens holder, a turbulence mechanism for inducing turbulence in the fluid, and an electronic control unit for operating the UV lamp and the turbulence mechanism in a single cleaning/disinfecting cycle of comparatively short duration. The lens holder has a pair of lower lens holder portions for the lenses and an upper bracket for shading the lenses form direct UV radiation. The turbulence mechanism is a magnetic pedal, tethered on the end of a flexible spring, which is driven by a magnetic flux generator to create a whirlpool in the fluid which swirls in and around the lens holder portion. Particles, films and other deposits dislodged from the lenses are carried by the whirlpool above the upper bracket of the lens holder where they are disinfected by the UV radiation. The pedal is driven in oscillation in a sub-sonic range of about 50–120 cyc/–sec. An electrical contact interlock between the upper housing and the lower base prevent accidental operation and irradiation by the UV lamp. The whirlpool turbulence cleans deposits form the lenses, thereby avoiding the need for manual scrubbing and detergent chemicals. The UV radiation disinfects the dislodged deposits and fluid quickly, without heating, and without the need for preservatives and disinfectant chemicals.

While these devices for cleaning contact lens may be suitable for the purposes for which they were designed, they would not be as suitable for the purposes of the present invention, as hereinafter described.

SUMMARY OF THE INVENTION

The present invention is a device for dislodging surface build-ups or contaminating films, whether protein or bacterial, which occur on soft contact lenses while being worn in the eyes by imparting a high amplitude, short duration force impulse to the lenses while placed within their contact lens storage case. Regular use of this device will extend the usable lens life over current methods of cleaning and storage. When the lenses are placed into their overnight storage container including storage solution, the container is placed into the device which when activated manually imparts a high amplitude, short duration shock to the lenses through the container and storage fluids. The shock dislodges substantially all surface contaminants and debris thereby extending the usable lens life.

An object of the present invention is to clean contact lens. A further object of the present invention is to provide a convenient method of cleaning contact lens. Yet another object of the present invention is to provide a device for leaning contact lens which is economical to manufacture. Another object of the present invention is to prevent the build-up of surface contamination on contact lens, A further object is to extend the useable wearable life of a set of contact lens.

The foregoing and other objects and advantages will appear from the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWINGS

In order that the invention may be more filly understood, it will now be described, by way of example, with reference to the accompanying drawings in which:

FIG. 4 is a cross-sectional view of another embodiment of the present invention showing the mechanical parts of the device.

FIG. 5 is a plan view of another embodiment of the present invention.

FIG. 6 is a cross-sectional view of the embodiment shown in FIG. 5 showing the mechanical parts of the device.

FIG. 7 is a crosssectional view of a contact lens storage case.

LIST OF REFERENCE NUMERALS

Figure 1:
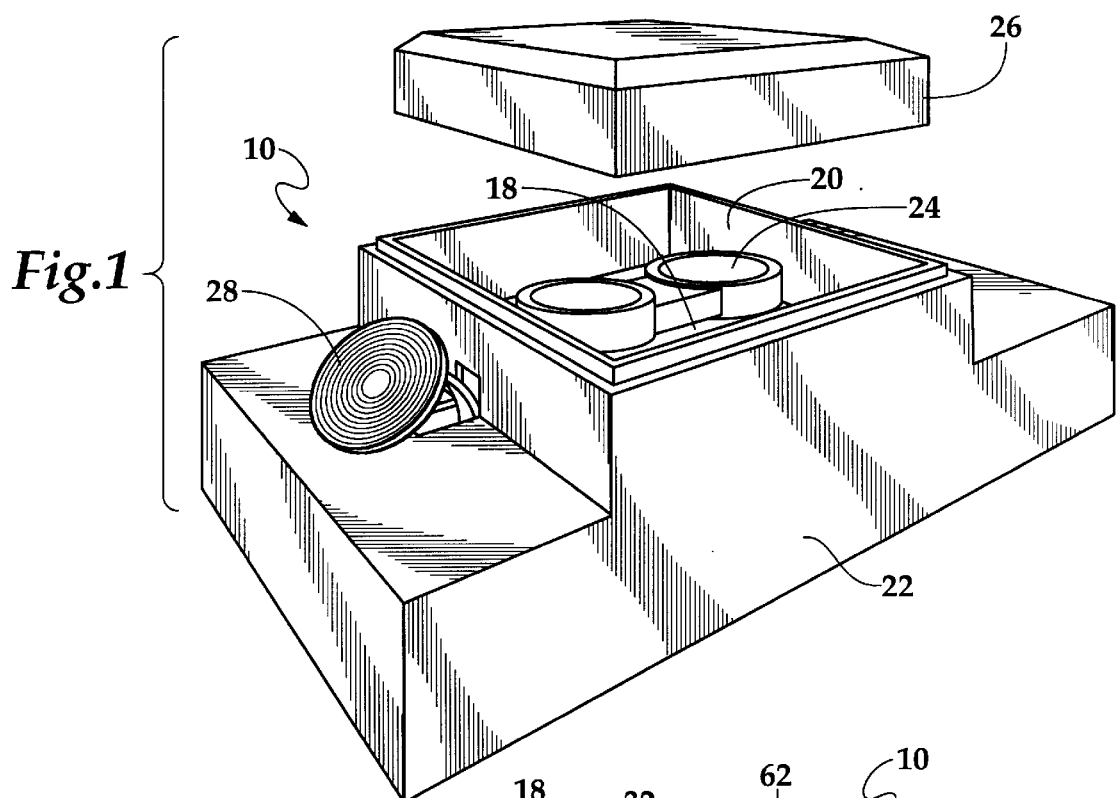
FIG. 1 is a perspective view of one embodiment of the present invention showing the placement of the contact lens storage case within the device.

With regard to reference numerals used, the following numbering is used the drawings.
10 present invention
12 spring
14 striking head
16 depressor lever
18 impact transmission plate
20 lens containment chamber
22 housing
24 contact lens storage case
26 cover
28 thumb depressor plate
30 direction arrow
32 contact lens
34 coil spring
35 rotary gear
36 teeth of gear
38 shaft
40 collar
42 spring
43 striking portion of spring
44 means for anchoring
46 finger
48 hole
50 first position
52 solution
54 lens case base member
56 lens case top
58 threaded attachment means
60 means for attaching plate
62 upper flange
64 lower flange
66 means for attaching spring
68 aperture
70 pivot pin
72 return spring
74 means for attachment
76 connecting member

DESCRIPTION OF THE PREFERRED EMBODIMENT(S)

Turning now descriptively to the drawings, in which similar reference characters denote similar elements throughout the several views, FIGS. 1 through 7 illustrate the present invention being a contact lens cleaner.

By way of overview of all embodiments of the present invention as shown in FIGS. 1 through 7, the present invention 10 is generally comprised of four major components: (1) an impact mechanism means comprised of a calibrated spring 12, impactor or striking head 14, and depressor lever 16; (2) an impact transmission plate 18 movably fixedly attached to the housing; (3) a lens containment chamber 20 with cover 26; and, (4) a housing 22 to secure the components in their respective positions. The lenses are placed in their storage case with solution for use with the present invention. In each embodiment, the impact springs are compressively arranged to deliver a force to the transmission plate 18.

Figure 2:
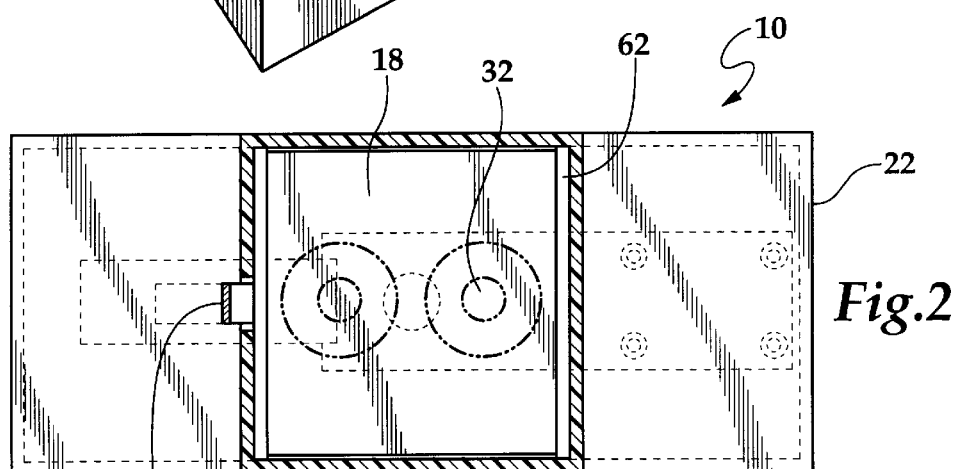
FIG. 2 is a plan view of the lens cleaning device of FIG. 1, taken from FIG. 3 as indicated.
Figure 3:
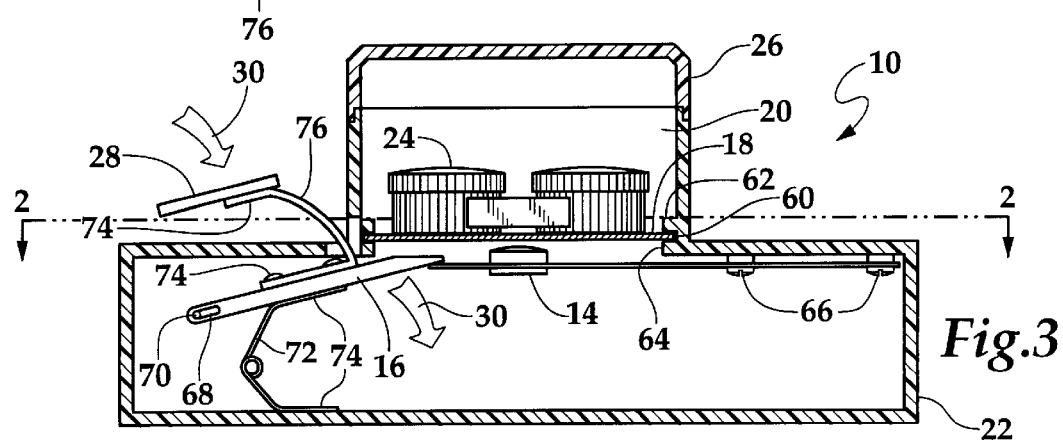
FIG. 3 is a cross-sectional view of the lens cleaning device of FIG. 1, taken between the edge and depressor lever of the device showing the mechanical parts of the device.

With reference to FIGS. 1 through 3, therein is shown the preferred embodiment of the lens cleaning device 10, showing the contact lens storage case 24 placed within the device 10 directly resting upon and in contact with the impact transmission plate 18 which forms the bottom of chamber 20. The cover 26 is then placed on the housing 22. The thumb depressor plate 28 when depressed downwardly as shown by direction arrow 30 moves the spring 12 and head 14 downwardly until the spring 12 is in a bent, tensioned configuration and thereafter the spring 12 is released. After release, spring 12 imparts a short, high force impulse to the transmission plate 18 which transmits, with minimal force dampening or distortion, the impact to the lens 32 through its case 24 and solution 52 (not shown, but see FIG. 7). The high intensity short duration shock is effectively strong so that it substantially cleans or loosens and dislodges protein and other types of build-up, e.g., bacteria, from the surface of soft contact lenses 32. Once dislodged, the loosened deposits remain suspended in the storage solution 52 (not shown, but see FIG. 7) and tends not to become reattached to the lens 32 surface. Transmission plate 18 is movably fixedly secured to the base 22 by means 60 comprising an upper 62 and lower 64 flanged member molded into base 22. Means 60 provides a small air gap above the transmission plate 18 when the plate 18 is at rest on the bottom flange 64 allowing the transmission plate 18 to be loosely held between flanges 62 and 64 so that the full force of the impact of the striking head 14 is transmitted through the plate 18 to the contact lens storage case 24 and not be absorbed by the housing 22. In practice, an air gap of about 2 mm has been found to function properly. Attachment means 66, e.g., screws, brads or the like, are provided for attaching spring 12 to base 22. In order to allow the tip of spring depressor lever 16 to clear the spring 12 after spring 12 is released back to its untensioned position generally parallel to the plate 18 from its downward tensioned position, a longitudinally elongated aperture 68 is provided in lever 16 so as to allow lever 16 to be movable backwardly and forwardly about its pivot pin 70 upon its flexible return spring member 72. Spring 72 has means for attachment 74 to lever 16 and base 22. A connecting member 76 connects plate 28 to lever 16 and also has means for attachment 74 to plate 28 and lever 16.

In use, after lens 32 removal from the eyes and placement securely within their storage case 24, the case 24 is placed on the impact plate 18 within chamber 20. The 13 cover 26 is placed on the chamber 20 and then the thumb depressor plate 28 is depressed imparting the high intensity shock to the lens 32. Lens cover 26 contains lens case 24 within chamber 20.

Turning to FIG. 4, therein is shown another embodiment of the lens cleaning device 10 utilizes a coil spring 34 and striking head 14 which is tensionally compressed and released by a rotary gear 35 having teeth 36 thereon to impart the required impact on the transmission plate 18. The gear 35 is rotated on a centrally positioned shaft 38 which is connected to a means for rotation (not shown) such as a hand actuated knob or lever situated on the outside of the housing 22. When rotated, the teeth 36 on the gear 35 are designed to engage the collar 40 at position A, compress the spring 34 and then release the spring 34 at position B, as the tooth 36 is rotated clear of the collar 40. The head 14 then strikes the transmission plate 18 with the required impact to dislodge the undesirable build up from the lens (not shown, but see FIG. 7) surfaces. The longitudinal axis of coil spring 34 is positioned generally perpendicular to plate 18. Note that an electrically actuated solenoid (not shown, but see FIG. 7) could be easily adapted to deliver the impact force in this configuration of the present invention 10. The solenoid could be designed as would be done by one skilled in the art in the standard manner.

In operation, the second embodiment of the present invention shown in FIG. 4, after lens 32 removal from the eyes and placement securely within the storage case 24 including overnight storage solution, the case 24 is placed on the transmission plate 18 within the chamber 20. The cover 26 is placed on the chamber 20 and operation of the impact head 14 is initiated by the knob or lever located on the outside of the housing 22.

Turning to FIGS. 5 and 6, shown therein is a third embodiment of the present invention, which shows the lens cleaning device 10 which utilizes a torsion spring 42 to impart the required impact on the transmission plate 18. The spring is anchored by means 44 at one end within the device housing 22 and the free end is configured to allow a striking portion 43 of the spring 42 to rest directly on the transmission plate 18. When the spring 42 is actuated with the finger 46 through a slotted hole 48 in the side of the housing 22 by depressing the spring 42 to a first position shown at 50 and thereafter releasing the spring 42 allowing the striking portion or head 43 of spring 42 to snap against the transmission plate 18 the required impact is sustained by the lens 32 (not shown, but see FIG. 7) dislodging the undesirable build up which occurs on the lens surfaces.

In operation, the third embodiment of this invention shown in FIGS. 5 and 6, after the lens removed from the eyes and placement securely within their storage container 24, including storage solution the container 24 is placed on the transmission plate 18 as in the other embodiments of this invention. The cover 26 is placed on the chamber 20. Then the spring 42 is actuated by hand using the finger 46 and hole 48 in the housing 22 imparting the required impact on the lenses (not shown, but see FIG. 7) to dislodge build up from the lens surfaces.

Turning to FIG. 7, shown therein a cross-sectional view of the contact lens storage case 24 showing the contact lens 32 inside in their customary soaking or cleaning solution 52 having a base member 54 and a top 56 having the customary threadable attachment means 58 as would be done by and designed by one skilled in the art in the standard manner. Contact lens storage case 24 is used to store the lens 32 for use with the present invention.

A laboratory bench scale study has been conducted on a model built according to the embodiment of the present invention 10 shown in FIGS. 1 through 3. Its spring imparted a force of about 17.6 pounds of force with t=0.001 seconds. Therefore it is believed that models built with at least this much impulse or energy capability would be effective to substantially clean contact lens according to the teachings of this specification. However, it is also believed that models built with less than this much impulse or energy capability would be effective to substantially clean contact lens according to the teachings of this specification.

What is claimed to be new and desired to be protected by Letters Patent is set forth in the appended claims:

I claim:

1. An apparatus for cleaning soft contact lenses while the soft contact lenses are placed in their customary liquid solution in a conventional contact lens storage case, comprising:
   a) a housing;
   b) a chamber within said housing, said chamber containing the contact lens storage case, the contact lens storage case containing the liquid solution and the contact lenses therein;
   c) a cover for said chamber for containing the contact lenses storage case within said chamber;
   d) an impact transmission plate for placement thereon of the contact lens storage case containing the contact lenses;
   e) said impact transmission plate forming the bottom of said chamber;
   f) means for transmitting an impulse to said impact transmission plate, said impulse being short and of high force; and,
   g) the contact lenses being substantially cleaned by said transmitted impulse.

2. The apparatus of claim 1, said means for striking further comprising a spring member.

3. The apparatus of claim 2, wherein said spring is a leaf spring, said leaf spring consisting of a single leaf.

4. The apparatus of claim 3, further comprising said leaf spring disposed parallel to said impact transmission plate, a striking head positioned on said leaf spring, means for urging said leaf spring away from said impact transmission plate, said leaf spring being disposed in a tensioned configuration, said leaf spring being freed from said tensioned configuration, said striking head of said leaf spring striking said impact transmission plate.

5. The apparatus of claim 4, said leaf spring striking said impact transmission plate effectively hard to clean the contact lenses.

6. The apparatus of claim 2, wherein said spring is a coil spring.

7. The apparatus of claim 6, further comprising said coil sprig having its longitudinal axis disposed perpendicular to said impact transmission plate, a striking head positioned on said coil spring, means for urging said coil spring away from said impact transmission plate, said coil spring being disposed in a tensioned configuration, said coil spring being freed from said tensioned configuration, said striking head of said coil spring striking said impact transmission plate.

8. The apparatus of claim 2, wherein said spring is a torsional spring.

9. The apparatus of claim 8, further comprising said torsional spring having one end member disposed parallel to said impact transmission plate, a striking portion configured on said torsional spring, means for urging said torsional spring away from said impact transmission plate, said torsional spring being disposed in a tensioned configuration, said torsional spring being freed from said tensioned configuration, said striking portion of said torsional spring striking said impact transmission plate.

10. The apparatus of claim 2, wherein said spring is compressively arranged to strike said impact transmission plate.

11. The apparatus of claim 1, said means for striking further comprising a solenoid.

12. The apparatus of claim 11, wherein said solenoid is positioned perpendicular to said impact transmission plate.

13. A method of cleaning soft contact lenses in their customary liquid solution in a conventional contact lens storage case, comprising the steps of:
   a) providing a housing having a chamber therein for holding the contact lens storage case containing the contact lenses;
   b) providing a cover on said chamber;
   c) placing the contact lens storage case containing the liquid solution and the contact lenses therein inside said chamber; and,
   d) transmitting a short high force impulse to the contact lens storage case.

14. A method of cleaning soft contact lenses in a conventional contact lens storage case, comprising the steps of:
   a) providing a housing having a chamber therein for holding therein the contact lens storage container case containing the contact lenses therein;
   b) providing a cover on said chamber;
   c) providing an impact transmission plate having the contact lens storage case positioned thereon; and,
   d) transmitting an impulse to the impact transmission plate said impulse having effective force to substantially clean the contact lenses.

15. An apparatus for cleaning soft contact lenses in a contact lens storage case, comprising:
   a) a housing;
   b) a chamber within said housing said chamber containing the contact lens storage case the contact lens storage case containing the liquid solution and the contact lenses therein;
   c) a cover for said chamber for assisting in containing the contact lens storage case within said chamber; and,
   d) means for transmitting an impulse to said contact lens storage case, said impulse being short and of high force, whereby the contact lenses are substantially cleaned.

* * * * *